(12) United States Patent
Artzi et al.

(10) Patent No.: US 10,342,894 B2
(45) Date of Patent: Jul. 9, 2019

(54) HYDROGEL COMPOSITES, COMPOSITIONS, AND METHODS

(71) Applicant: Massachusetts Institute of Technology, Cambridge, MA (US)

(72) Inventors: Natalie Artzi, Brookline, MA (US); Elazer Reuven Edelman, Brookline, MA (US); Shimon Aryeh Unterman, Brookline, MA (US); Lyndon Fitzgerald Charles, Somerville, MA (US); Sara Elaine Strecker, Wethersfield, CT (US)

(73) Assignee: Massachusetts Institute of Technology, Cambridge, MA (US)

( * ) Notice: Subject to any disclaimer, the term of this patent is extended or adjusted under 35 U.S.C. 154(b) by 121 days.

(21) Appl. No.: 15/293,522

(22) Filed: Oct. 14, 2016

(65) Prior Publication Data
US 2017/0106117 A1    Apr. 20, 2017

Related U.S. Application Data

(60) Provisional application No. 62/242,511, filed on Oct. 16, 2015.

(51) Int. Cl.
| | | |
|---|---|---|
| *A61L 24/00* | (2006.01) | |
| *A61L 24/04* | (2006.01) | |
| *A61L 26/00* | (2006.01) | |
| *A61L 27/44* | (2006.01) | |
| *A61L 27/52* | (2006.01) | |

(52) U.S. Cl.
CPC ....... *A61L 26/0052* (2013.01); *A61L 24/0089* (2013.01); *A61L 24/043* (2013.01); *A61L 26/0004* (2013.01); *A61L 26/008* (2013.01); *A61L 26/0019* (2013.01); *A61L 26/0057* (2013.01); *A61L 26/0066* (2013.01); *A61L 27/446* (2013.01); *A61L 27/52* (2013.01); *A61L 2400/06* (2013.01); *A61L 2430/02* (2013.01); *A61L 2430/06* (2013.01)

(58) Field of Classification Search
CPC .. A61L 26/0052; A61L 27/446; A61L 24/043; A61L 24/0089; A61L 27/52; A61L 26/0004; A61L 26/0057; A61L 26/008; A61L 26/0066; A61L 2400/06
See application file for complete search history.

(56) References Cited

U.S. PATENT DOCUMENTS

| | | |
|---|---|---|
| 2010/0016886 A1 | 1/2010 | Lu |
| 2011/0189291 A1* | 8/2011 | Yang et al. |
| 2011/0275572 A1 | 11/2011 | Rafailovich et al. |

FOREIGN PATENT DOCUMENTS

WO    2012/142470 A1    10/2012

OTHER PUBLICATIONS

Ghadiri et al., Applied Clay Science, 2013, vol. 85, p. 64-73.*
Maiti et al., Chem. Mater, 2002, vol. 14, p. 4654-4661.*
PCT International Search Report and Written Opinion for PCT Application No. PCT/US2016/056967 dated Feb. 3, 2017 (14 pages).
Nistor et al., "Hybrid Collagin-Based Hydrogels with Embedded Montmorillonite Nanoparticles," Materials Science and Engineering, 2015, C53:212-221.
Segovia et al., "Hydrogel Doped with Nanoparticles for Local Sustained Release of SiRNA in Breast Cancer," Adv. Healthcare Mater., 2015, 4:271-280.
Database WPI, XP002765799, Thomson Scientific, 2013, Abstract (2 pages).
Database WPI, XP0027565800, Thomson Scientific, 2013, Abstract (2 pages).

* cited by examiner

*Primary Examiner* — Kade Ariani
(74) *Attorney, Agent, or Firm* — Eversheds Sutherland (US) LLP (57) ABSTRACT

Provided herein are methods for treating, adhering, or sealing biological tissue with a material, such as a hydrogel, that may include phyllosilicate nanoplatelets. The phyllosilicate nanoplatelets can have a high aspect ratio, a low aspect ratio, or be a mixture of high aspect ratio and low aspect ratio nanoplatelets. Drug releasing compositions and kits also are provided herein.

33 Claims, 5 Drawing Sheets

HYDROGEL COMPOSITES, COMPOSITIONS, AND METHODS

CROSS-REFERENCE TO RELATED APPLICATIONS

This application claims priority to U.S. Provisional Patent Application No. 62/242,511, filed Oct. 16, 2015, which is incorporated herein by reference.

BACKGROUND

Hydrogels, primarily due to their relatively high water content, have been used in tissue engineering and drug delivery, and can allow for nearly free diffusion of drugs and/or nutrients. Hydrogels can be modified readily with a range of chemical functionalities, which may impart at least one of bioactivity, controlled degradability, and a variety of pore sizes.

Hydrogels also can be advantageous due to their ability to be injected in a fluid state, conform to the shape of a tissue, and/or be solidified in situ using a variety of chemical and physical crosslinking methodologies. The crosslinking methods often can be extended to create hydrogels that are cohesive and capable of adhering to a surrounding tissue, thereby possibly enhancing tissue-biomaterial integration.

Hydrogels, however, generally have weak mechanical properties, e.g., modulus, toughness, and/or strength, compared to many biological tissues. Most hydrogels are quite brittle and weak. Although the modern material design of some hydrogels has been aimed at improving toughness and stiffness through the use of composites, the resulting hydrogels still tend to be too weak for mechanically demanding applications within the body. As a result, hydrogels frequently are applied only to softer tissues. Also, some injected hydrogels flow too readily prior to gelation, thereby complicating their implantation in wet conditions or in difficult geometries.

There exists a need for hydrogels that have mechanical properties that permit their use with a number of different tissues in a variety of locations.

BRIEF SUMMARY

Provided herein are methods for treating, adhering, or sealing biological tissue. In embodiments, the methods comprise providing a first solution comprising a first polymer component comprising a first polymer having one or more aldehydes; providing a second solution comprising at least one of (i) a dendrimer comprising at least two branches with one or more surface groups, wherein about 25% to 100% of the surface groups comprise at least one primary or secondary amine, and (ii) a second polymer component comprising a second polymer having one or more amines; combining the first and second solutions together to produce a hydrogel composite; and contacting one or more biological tissues with the hydrogel composite, wherein at least one of the first solution and the second solution comprises phyllosilicate nanoplatelets.

Also provided herein are kits for making a hydrogel composite. In embodiments, the kits comprise a first part that includes a first solution comprising a first polymer component comprising a first polymer having one or more aldehydes; and a second part that includes a second solution comprising at least one of (i) a dendrimer comprising at least two branches with one or more surface groups, wherein about 25% to 100% of the surface groups comprise at least one primary or secondary amine, and (ii) a second polymer component comprising a second polymer having one or more amines, wherein at least one of the first solution and the second solution comprises phyllosilicate nanoplatelets. The kits may comprise a syringe in which the first solution and the second solution are stored. The syringe may include a mixing tip.

Also provided herein are drug delivery compositions. The drug delivery compositions, in embodiments, comprise a first solution comprising a first polymer component comprising a first polymer having one or more aldehydes; a second solution comprising at least one of (i) a dendrimer comprising at least two branches with one or more surface groups, wherein about 25% to 100% of the surface groups comprise at least one primary or secondary amine, and (ii) a second polymer component comprising a second polymer having one or more amines; and at least one drug in at least one of the first solution and the second solution, wherein at least one of the first solution and the second solution comprises phyllosilicate nanoplatelets.

Also provided herein are methods for local delivery of a drug to a biological tissue. The methods for local delivery of a drug to a biological tissue may comprise applying to a biological tissue a drug delivery composition as provided herein; and permitting the at least one drug to diffuse from the composition into the biological tissue.

DETAILED DESCRIPTION

Improved hydrogel composites, compositions, such as drug delivery compositions, and methods have been developed for adhering, sealing, or treating one or more biological tissues. Generally, the hydrogel composites and compositions provided herein are formed from one or more solutions comprising phyllosilicate nanoplatelets.

The hydrogel composites and compositions provided herein may have improved rheological and/or mechanical properties, because the hydrogel composites and compositions provided herein are formed from one or more solutions comprising phyllosilicate nanoplatelets. The phyllosilicate nanoplatelets, in some embodiments, also can help to control one or more of [1] mass loss from the hydrogel composites and compositions, [2] drug release through interactions with drugs or drug-conjugated polymers, or changes in diffusivity, and [3] cell-material and tissue-material interactions through changes to cell adhesion, morphology, and biology, or [4] a combination thereof.

Generally, in embodiments, the hydrogel composites and compositions may be used on or in any amine-containing surface or area. For example, the hydrogel composites and compositions may be used on or in any internal or external biological tissues, lumens, orifices, or cavities. The biological tissues, lumens, orifices, or cavities may be human or other mammalian tissues, lumens, orifices, or cavities. The biological tissues may be natural or artificially generated. Therefore, the biological tissues may be in vivo or in vitro. The biological tissues may be skin, bone, ocular, muscular, vascular, or an internal organ, such as lung, intestine, heart, liver, etc.

In some embodiments, the hydrogel composites and compositions serve as a matrix material for controlled release of drug. In other embodiments, the hydrogel composites and compositions may be used in medical applications as a scaffold, filler, prosthetic, artificial tissue, or a combination thereof. The hydrogel composites and compositions can be applied to a tissue site in a human or other animal patient, for example, during a surgical or other medical procedure. In one embodiment, the hydrogel composites and compositions are used to create an anastomosis. In particular embodiments, the hydrogel composites and compositions are used to adhere, seal, and/or treat a wound, lesion, or a combination thereof. For example, the hydrogel composites and compositions may be applied to slow-healing or troublesome wounds, such as those suffered by diabetics. In one embodiment, the hydrogel composites and compositions may be used to secure or help secure a medical implant, such as an orthopedic implant, within a human or other animal patient.

Hydrogel Composites and Compositions

Generally, the hydrogel composites and compositions, including drug delivery compositions, provided herein may be formed by combining a first solution and a second solution as described herein. The first solution and the second solution may be aqueous macromer solutions. The first solution and/or the second solution may independently include water, phosphate buffer saline (PBS), Dulbecco's Modified Eagle's Medium (DMEM), or any combination thereof.

The first solution, in embodiments, comprises phyllosilicate nanoplatelets and a first polymer component. The first solution, in other embodiments, comprises a first polymer component without phyllosilicate nanoplatelets. The first polymer component generally includes a first polymer with one or more functional groups capable of reacting with one or more functional groups on a biological tissue and/or one or more functional groups on a dendrimer and/or second polymer component of a second solution. The first polymer, in some embodiments, includes a polymer having one or more aldehyde groups.

The second solution may comprise at least one of a dendrimer and a second polymer component. The dendrimer and/or second polymer component generally have one or more functional groups capable of reacting with the one or more functional groups on the first polymer. The dendrimer and/or second polymer component, in particular embodiments, include one or more amines. The second solution, in other embodiments, also comprises phyllosilicate nanoplatelets.

The first solution and the second solution, in embodiments, are combined to form the hydrogel composites and compositions described herein. When combined, the aldehyde groups of the first solution may react with the amines that are present in the second solution. This reaction is referred to herein as "curing" or "gelling."

In embodiments, the phyllosilicate nanoplatelets are present in the first solution. In some embodiments, the phyllosilicate nanoplatelets are present in the first solution and the second solution. In further embodiments, the phyllosilicate nanoplatelets are present in the second solution. When the first solution and the second solution comprise phyllosilicate nanoplatelets, the phyllosilicate nanoplatelets of the first solution and the second solution may have the same or different compositions, and/or the same or different sizes/shapes. For example, the first solution may comprise nanoplatelets having a low aspect ratio, and the second solution may comprise nanoplatelets having a high aspect ratio or a mixture of high and low aspect ratio nanoplatelets, or vice versa.

In embodiments, the phyllosilicate nanoplatelets are substantially evenly dispersed in the first solution. In other embodiments, the phyllosilicate nanoplatelets are substantially evenly dispersed in the first solution and the second solution. In further embodiments, the phyllosilicate nanoplatelets are evenly dispersed in the second solution. Although the phyllosilicate nanoplatelets are evenly dispersed in preferred embodiments, other embodiments may not have an even dispersement of the phyllosilicate nanoplatelets.

In embodiments, the concentration of phyllosilicate nanoplatelets in the first solution, the second solution, or in the first solution and second solution, may be adjusted independently to achieve a range of mechanical properties.

In embodiments, the concentration of phyllosilicate nanoplatelets in the first solution is about 0.01% to about 30% by weight of the first solution. In some embodiments, the concentration of phyllosilicate nanoplatelets in the first solution is about 0.01% to about 25% by weight of the first solution. In further embodiments, the concentration of phyllosilicate nanoplatelets in the first solution is about 0.01% to about 20% by weight of the first solution. In still further embodiments, the concentration of phyllosilicate nanoplatelets in the first solution is about 0.01% to about 15% by weight of the first solution.

In embodiments, the concentration of phyllosilicate nanoplatelets in the second solution is about 0.01% to about 30% by weight of the second solution. In some embodiments, the concentration of phyllosilicate nanoplatelets in the second solution is about 0.01% to about 25% by weight of the second solution. In further embodiments, the concentration of phyllosilicate nanoplatelets in the second solution is about 0.01% to about 20% by weight of the second solution. In still further embodiments, the concentration of phyllosilicate nanoplatelets in the second solution is about 0.01% to about 15% by weight of the second solution.

In embodiments, the concentration of the phyllosilicate nanoplatelets in the hydrogel composites or compositions described herein is about 0.01% to about 10% by weight of the hydrogel composite or composition. In some embodiments, the concentration of the phyllosilicate nanoplatelets in the hydrogel composites or compositions described herein is about 0.01% to about 8% by weight of the hydrogel composite or composition. In certain embodiments, the concentration of the phyllosilicate nanoplatelets in the hydrogel composites or compositions described herein is about 0.01% to about 6% by weight of the hydrogel composite or composition. In particular embodiments, the concentration of the phyllosilicate nanoplatelets in the hydrogel composites or compositions described herein is about 0.01% to about 5% by weight of the hydrogel composite or composition.

In embodiments, the concentration of first polymer component in the first solution is about 0.01% to about 40% by weight of the first solution. In further embodiments, the concentration of first polymer component in the first solution is about 0.01% to about 30% by weight of the first solution. In some embodiments, the concentration of first polymer component in the first solution is about 0.01% to about 20% by weight of the first solution. In a particular embodiment, the concentration of first polymer component in the first solution is about 20% by weight of the first solution. In additional embodiments, the concentration of first polymer component in the first solution is about 0.01% to about 10% by weight of the first solution. Typically, the concentration may be tailored and/or adjusted based on the particular application, tissue type, and/or the type and concentration of dendrimer and/or second polymer component used.

In embodiments, the concentration of the first polymer component in the hydrogel composites or compositions described herein is about 0.01% to about 20% by weight of the hydrogel composite or composition. In further embodiments, the concentration of the first polymer component in the hydrogel composites or compositions described herein is about 0.01% to about 15% by weight of the hydrogel composite or composition. In some embodiments, the concentration of the first polymer component in the hydrogel composites or compositions described herein is about 0.01% to about 10% by weight of the hydrogel composite or composition. In still further embodiments, the concentration of the first polymer component in the hydrogel composites or compositions described herein is about 0.01% to about 7% by weight of the hydrogel composite or composition.

In embodiments, the total concentration of dendrimer and second polymer component in the second solution is about 0.01% to about 40% by weight of the second solution. In further embodiments, the total concentration of dendrimer and second polymer component in the second solution is about 0.01% to about 30% by weight of the second solution. In some embodiments, the total concentration of dendrimer and second polymer component in the second solution is about 0.01% to about 20% by weight of the second solution. In additional embodiments, the total concentration of dendrimer and second polymer component in the second solution is about 0.01% to about 10% by weight of the second solution. In a particular embodiment, the total concentration of dendrimer and second polymer component in the second solution is about 25% by weight of the second solution. Typically, the concentration may be tailored and/or adjusted based on the particular application, tissue type, and/or the type and concentration of first polymer component used. As used herein, the phrase "total concentration of dendrimer and second polymer component" refers to the sum of the concentration of dendrimer and the concentration of the second polymer component. The phrase does not imply that both a dendrimer and a second polymer component must be present in the second solution. The second solution may include a dendrimer, second polymer component, or both a dendrimer and second polymer component.

In embodiments, the total concentration of dendrimer and second polymer component in the hydrogel composites or compositions described herein is about 0.01% to about 20% by weight of the hydrogel composite or composition. In further embodiments, the total concentration of dendrimer and second polymer component in the hydrogel composites or compositions described herein is about 0.01% to about 15% by weight of the hydrogel composite or composition. In some embodiments, the total concentration of dendrimer and second polymer component in the hydrogel composites or compositions described herein is about 0.01% to about 10% by weight of the hydrogel composite or composition. In still further embodiments, the total concentration of dendrimer and second polymer component in the hydrogel composites or compositions described herein is about 0.01% to about 7% by weight of the hydrogel composite or composition.

Phyllosilicate Nanoplatelets

Phyllosilicate nanoplatelets are well known in the art, and generally are phyllosilicate materials having a high surface area to volume ratio.

Not wishing to be bound by any particular theory, it is believed, in some embodiments, that the high surface area of phyllosilicate nanoplatelets allows for a significant number of favorable interactions between the phyllosilicate nanoplatelets and a matrix, such as a polymeric matrix, thereby enhancing modulus, mechanical stiffness, resistance to fracture, strength, and/or resistance to deformation prior to curing or gelling.

It is believed that the noncovalent interactions between the phyllosilicate nanoplatelets and the polymers of the first solution or first and second solutions cause the solutions to exhibit significant shear thinning and Bingham fluid properties prior to curing or gelling. At low shear stresses, the first solution or first and second solutions may not flow and behave as elastic solids until a yield stress is reached, after which they will flow more readily. In addition, at low shear stresses the first solution or the first and second solutions may exhibit high viscosities and flow slowly, but may readily flow upon application of higher shear rates, such as those found during mixing and injection. This feature can be advantageous because the hydrogel composites and compositions described herein may not behave like traditional injectable materials, which are difficult to control during use because they continue to flow after injection. The hydrogel composites and compositions provided herein may flow after injection, but remain moldable prior to the substantial completion of curing or gelling. This feature may permit the hydrogel composites and compositions to have a number of uses, including those described herein, and be used in a variety of implantation locations.

Also, it is believed that the aspect ratio and shape of phyllosilicate nanoplatelets allows them to impart rheological improvements.

In embodiments, the phyllosilicate nanoplatelets comprise exfoliated phyllosilicate nanoplatelets.

In embodiments, the phyllosilicate nanoplatelets comprise one or more natural clays. In some embodiments, the phyllosilicate nanoplatelets comprise one or more synthetic clays. In further embodiments, the phyllosilicate nanoplatelets comprise one or more natural clays and one or more synthetic clays.

In embodiments, the phyllosilicate nanoplatelets comprise natural smectite clays, such as montmorillonite. In some embodiments, the phyllosilicate nanoplatelets comprise synthetic hectorite, e.g., Laponite.

In embodiments, the phyllosilicate nanoplatelets are substituted. The substituents may be selected to adjust the hydrophilicity, hydrophobicity, charge, chemical functionalization, or a combination thereof. In some embodiments, at least a portion of the phyllosilicate nanoplatelets is substituted with functionalized cations. In particular embodiments, at least a portion of the phyllosilicate nanoplatelets is substituted with alkylammonium cations.

Not wishing to be bound by any particular theory, it is believed that the rheological and mechanical properties of the first solution, the second solution, the hydrogel composites, and the compositions provided herein can be adjusted independently by altering at least one of the platelet size, aspect ratio, and/or type of the phyllosilicate nanoplatelets.

In embodiments, the phyllosilicate nanoplatelets in the first solution have a high aspect ratio. In other embodiments, the phyllosilicate nanoplatelets in the first solution have a low aspect ratio. In further embodiments, the first solution comprises phyllosilicate nanoplatelets having a high aspect ratio and phyllosilicate nanoplatelets having a low aspect ratio.

In embodiments, the phyllosilicate nanoplatelets in the second solution have a high aspect ratio. In other embodiments, the phyllosilicate nanoplatelets in the second solution have a low aspect ratio. In further embodiments, the second solution comprises phyllosilicate nanoplatelets having a high aspect ratio and phyllosilicate nanoplatelets having a low aspect ratio.

As used herein, the phrase "aspect ratio" refers to the ratio of the largest dimension of a surface of a phyllosilicate nanoplatelet to the thickness of the phyllosilicate nanoplatelet. For a plurality of phyllosilicate nanoplatelets, the average largest dimension of the surfaces of the phyllosilicate nanoplatelets, and the average thickness of the phyllosilicate nanoplatelets may be used to determine the aspect ratio.

A phyllosilicate nanoplatelet having a "high aspect ratio" is one in which the aspect ratio is at least 80:1. In embodiments, the high aspect ratio phyllosilicate nanoplatelets have an aspect ratio of 80:1 to about 1,000:1. In another embodiment, the high aspect ratio phyllosilicate nanoplatelets have an aspect ratio of 80:1 to about 500:1. In a further embodiment, the high aspect ratio phyllosilicate nanoplatelets have an aspect ratio of about 100:1 to about 500:1. In yet another embodiment, the high aspect ratio phyllosilicate nanoplatelets have an aspect ratio of about 100:1 to about 200:1.

A phyllosilicate nanoplatelet having a "low aspect ratio" is one in which the aspect ratio is less than or equal to 40:1. In embodiments, the low aspect ratio phyllosilicate nanoplatelets have an aspect ratio of about 10:1 to 40:1. In one embodiment, the low aspect ratio phyllosilicate nanoplatelets have an aspect ratio of about 15:1 to 40:1. In a further embodiment, the low aspect ratio phyllosilicate nanoplatelets have an aspect ratio of about 20:1 to 40:1. In yet another embodiment, the low aspect ratio phyllosilicate nanoplatelets have an aspect ratio of about 20:1 to 30:1.

The phyllosilicate nanoplatelets may have one or more surfaces that are at least substantially square shaped, substantially circular, or a combination thereof. In one embodiment, the phyllosilicate nanoplatelets are low aspect ratio phyllosilicate nanoplatelets having one or more surfaces that are at least substantially square, at least substantially circular, or a combination thereof. In one embodiment, the phyllosilicate nanoplatelets are high aspect ratio phyllosilicate nanoplatelets having one or more surfaces that are at least substantially square, at least substantially circular, or a combination thereof.

The phyllosilicate nanoplatelets may have a thickness of about 0.8 nm to about 1.2 nm. In one embodiment, the phyllosilicate nanoplatelets have a thickness of about 1 nm. In one embodiment, the phyllosilicate nanoplatelets are low aspect ratio phyllosilicate nanoplatelets having an average thickness of about 0.8 nm to about 1.2 nm, and the average largest dimension of the surfaces of the phyllosilicate nanoplatelets is about 20 nm to about 30 nm. In another embodiment, the phyllosilicate nanoplatelets are high aspect ratio phyllosilicate nanoplatelets having an average thickness of about 0.8 nm to about 1.2 nm, and the average largest dimension of the surfaces of the phyllosilicate nanoplatelets is about 100 nm to about 200 nm.

Not wishing to be bound by any particular theory, it is believed that phyllosilicate nanoplatelets having a low aspect ratio can increase shear thinning and/or yield stresses of the first solution, the second solution, or the first solution and the second solution. For example, in embodiments, adding to the first solution phyllosilicate nanoplatelets having a low aspect ratio in an amount of about 0.01% to about 8.0% by weight of the first solution can increase shear thinning and yield stresses of the first solution.

Not wishing to be bound by any particular theory, it is believed that phyllosilicate nanoplatelets having a high aspect ratio can increase the elastic modulus and/or strength of the hydrogel composites and compositions described herein. For example, in embodiments, the elastic modulus and strength of the hydrogel composites and compositions can be improved by adding phyllosilicate nanoplatelets having a high aspect ratio to the first solution, the second solution, or the first solution and second solution in an amount of about 0.01% to about 10% by weight of the hydrogel composite or composition.

In embodiments, the phyllosilicate nanoplatelets have surfaces bearing a net negative charge. It is believed that this feature may allow the phyllosilicate nanoplatelets to exhibit a high cation exchange capacity. This cation exchange capacity can be beneficial for at least two reasons. First, it can be harnessed, in some embodiments, to alter the interaction between a polymer component and the phyllosilicate nanoplatelets. Second, it can allow the phyllosilicate nanoplatelets to be used as a reservoir for cationic drugs, biologics, or a combination thereof. This feature combined with the large surface area of the phyllosilicate nanoplatelets may permit for high drug loadings, and/or the sustained release of drugs, growth factors, other bioactive factors, or a combination thereof. The unique charge, shape, and/or size of the phyllosilicate nanoplatelets may provide an anchor for cells or cell-deposited matrix molecules.

In embodiments, the phyllosilicate nanoplatelets are bioactive. The term "bioactive," as used herein, means that the phyllosilicate nanoplatelets contribute to the treating, adhering, or sealing of biological tissue, or impart some other positive benefit to biological tissue. For example, recent studies have demonstrated that phyllosilicate nanoplatelets may enhance bone formation. The dissolution products of some silicates, such as silicon, magnesium, and lithium, are known to be bioactive, and, therefore, can be used to tune the biological response to an implanted hydrogel composite or composition.

First Polymer Component

The first polymer component generally includes a first polymer with one or more functional groups capable of reacting with one or more functional groups on a biological tissue and/or one or more functional groups on the dendrimer and/or second polymer component of the second solution. The first polymer component, in embodiments, comprises a first polymer having one or more aldehyde groups.

The polymers of the first polymer component may be selected from any biocompatible polymers capable of forming or imparting certain characteristics to the hydrogel composites and compositions described herein. The polymers of the first polymer component, for example, may be selected from at least one polysaccharide, at least one hydrophilic polymer, at least one hydrophobic polymer, or combinations thereof.

In one embodiment, the first polymer component includes a first polymer that is a polysaccharide having one or more aldehyde groups. In a certain embodiment, the first polymer component includes a first polymer that is a hydrophilic polymer having one or more aldehyde groups. In another embodiment, the first polymer component includes a first polymer that is a polysaccharide having one or more aldehyde groups, and a hydrophilic polymer. In further embodiments, the first polymer component includes a first polymer that is a polysaccharide having one or more aldehyde groups, a hydrophilic polymer, and a hydrophobic polymer. In some embodiments, the first polymer component comprises a first polymer that includes a polysaccharide and a hydrophilic polymer, wherein both the polysaccharide and hydrophilic polymer have one or more aldehyde groups. Therefore, as used herein, the phrase "first polymer" refers to the one or more polymers of the first polymer component that include one or more functional groups, e.g., aldehydes, that are capable of reacting with a biological tissue and/or the functional groups of the dendrimer or second polymer component. In still further embodiments, the first polymer component comprises a first polymer that includes a polysaccharide and a hydrophilic polymer, wherein both the polysaccharide and hydrophilic polymer have one or more aldehyde groups, and a hydrophobic polymer.

In embodiments, the first polymer comprises at least one polysaccharide. The at least one polysaccharide may be linear, branched, or have both linear and branched sections within its structure. The at least one polysaccharide may be anionic, cationic, nonionic, or a combination thereof. Generally, the at least one polysaccharide may be natural, synthetic, or modified—for example, by crosslinking, altering the polysaccharide's substituents, or both. In one embodiment, the at least one polysaccharide is plant-based. In another embodiment, the at least one polysaccharide is animal-based. In yet another embodiment, the at least one polysaccharide is a combination of plant-based and animal-based polysaccharides. Non-limiting examples of polysaccharides include, but are not limited to, dextran, dextrin, chitin, starch, agar, cellulose, hyaluronic acid, derivatives thereof, such as cellulose derivatives, or a combination thereof.

In embodiments, the at least one polysaccharide is non-ionic. Non-limiting examples of nonionic polysaccharides include dextran, dextrin, and cellulose derivatives. In other embodiments, the at least one polysaccharide is anionic. Non-limiting examples of anionic polysaccharides include hyaluronic acid, chondroitin sulfate, alginate, and cellulose gum. In further embodiments, the at least one polysaccharide is cationic. The cationic character may be imparted by substituting the at least one polysaccharide with positively charge groups, such as trimethylammonium groups. Non-limiting examples of cationic polysaccharides include chitosan, cationic guar gum, cationic hydroxyethylcellulose, or other polysaccharides modified with trimethylammonium groups to confer positive charge.

In embodiments, the first polymer component comprises one or more hydrophilic polymers. The hydrophilic polymers are modified, in some embodiments, to confer degradability. For example, the hydrophilic polymers may be modified with polyester groups in order to impart degradability of the hydrophilic polymer. In particular embodiments, the hydrophilic polymers are substituted with one or more functional groups, such as aldehydes, that are capable of reacting with biological tissue and/or the functional groups of the dendrimer and/or second polymer component, such as amines. Generally, any biocompatible hydrophilic polymer may be used. Non-limiting examples of hydrophilic polymers include poly(vinyl alcohol), poly(acrylic acid), poly(acrylamide), poly(ethylene oxide), or combinations thereof.

In embodiments, the first polymer component comprises one or more hydrophobic polymers. The hydrophobic polymers may be modified with pendant hydrophilic polymers to adjust their characteristics. Non-limiting examples of hydrophobic polymers include polycaprolactam, poly(lactic acid), polycaprolactone, or combinations thereof. In some embodiments, hydrophobic polymers can be added to the phyllosilicate nanoplatelets using a hot melt process rather than a solvation process.

In certain embodiments, the first polymer has a molecular weight of about 1,000 to about 1,000,000 Daltons. In one embodiment, the first polymer has a molecular weight of about 5,000 to about 15,000 Daltons. Unless specified otherwise, the "molecular weight" of the polymer refers to the number average molecular weight. The molecular weight may be adjusted to attain certain properties, as known to those of skill in the art.

Generally, the one or more functional groups of the first polymer may be present in a number sufficient to form the hydrogel composites and compositions described herein. In certain embodiments, the first polymer's degree of functionalization is adjustable. The "degree of functionalization" generally refers to the number or percentage of groups on the polymer that are replaced or converted to the desired one or more functional groups. The one or more functional groups, in particular embodiments, include aldehydes. In one embodiment, the degree of functionalization is adjusted based on the type of tissue to which the hydrogel composites or compositions is applied, the concentration(s) of the various components, and/or the type of polymer(s) or dendrimer(s) used in the first and second solutions. In one embodiment, the degree of functionalization is about 10% to about 75%. In another embodiment, the degree of functionalization is about 25% to about 60%. In yet another embodiment, the degree of functionalization is about 40% to about 50%.

In one embodiment, the first polymer is a polysaccharide having about 10% to about 75% of its vicinal hydroxyl groups converted to aldehydes. In another embodiment, the first polymer is a polysaccharide having about 25% to about 75% of its vicinal hydroxyl groups converted to aldehydes.

In one embodiment, the first polymer is dextran with a molecular weight of about 10 kDa. In another embodiment, the first polymer is dextran having about 50% of its vicinal hydroxyl group converted to aldehydes. In a further embodiment, the first polymer is dextran with a molecular weight of about 10 kDa and about 50% of its vicinal hydroxyl groups converted to aldehydes.

In some embodiments, a polysaccharide and/or hydrophilic polymer is oxidized to include a desired percentage of one or more aldehyde functional groups. Generally, this oxidation may be conducted using any known means. For example, suitable oxidizing agents include, but are not limited to, periodates, hypochlorites, ozone, peroxides, hydroperoxides, persulfates, and percarbonates. In one embodiment, the oxidation is performed using sodium periodate. Typically, different amounts of oxidizing agents may be used to alter the degree of functionalization. In addition to, or independently of, other methods, aldehyde groups can be grafted onto the polymer backbone using known bioconjugation techniques in the event that oxidative methods are unsuitable.

The first solution may also include one or more additives. In one embodiment, the additive is compatible with the first polymer component and phyllosilicate nanoplatelets. In another embodiment, the additive does not contain primary or secondary amines. Generally, the amount of additive varies depending on the application, tissue type, concentration of the first solution, concentration of the second solution, the type of first polymer component, the type of dendrimer, and/or the type of second polymer component. Examples of suitable additives, include, but are not limited to, pH modifiers, thickeners, antimicrobial agents, colorants, surfactants, radio-opaque compounds, bioactive agents, adhesion ligands, and the other additives described herein. In other embodiments, first solution comprises a foaming agent.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water. In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the first solution includes one or more drugs. In such embodiments, the hydrogel composites or compositions may serve as a matrix material for controlled release of drug. The drug may be essentially any drug suitable for local, regional, or systemic administration from a quantity of the hydrogel composite or composition that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicylic acid acetate, ibuprophen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. In a particular embodiment, the drug comprises human bone morphogenetic protein 2. Other drugs are envisioned.

In other particular embodiments, the first solution includes one or more cells. For example, the hydrogel composite or composition may serve as a matrix material for delivering cells to a tissue site at which the hydrogel composite or composition has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Second Polymer Component

The second polymer component generally includes a second polymer with one or more functional groups capable of reacting with one or more functional groups of the first polymer of the first polymer component. The second polymer component, in embodiments, comprises a second polymer having one or more amines. The amines may be primary amines, secondary amines, or a combination thereof.

The polymers of the second polymer component may be selected from any biocompatible polymers capable of forming or imparting certain characteristics to the hydrogel composites and compositions described herein. The polymers of the second polymer component, for example, may be selected from at least one biopolymer, polyamine, or a combination thereof.

In one embodiment, the second polymer component includes a second polymer that is a biopolymer having one or more amines, such as primary amines, secondary amines, or a combination thereof. Non-limiting examples of biopolymers include chitosan, collagen, gelatin, other structural biomolecules, or a combination thereof. In a particular embodiment, the second polymer comprises a polyamine. The polyamine may be synthetic. Non-limiting examples of polyamines include amine-terminated, multi-arm poly(ethylene oxide) and polyethyleneimine. In another embodiment, the second polymer component includes a second polymer that comprises both (i) a biopolymer having one or more amines, and (ii) a polyamine. Therefore, as used herein, the phrase "second polymer" refers to the one or more polymers of the second polymer component that include one or more functional groups, e.g., amines, that are capable of reacting with the one or more functional groups of the first polymer component, such as aldehydes.

In some embodiments, the second polymer is a commercially available amine-terminated polymer, such as Type I collagen, Type II collagen, Type III collagen, gelatin that is acid- or base-catalyzed (i.e., Type A or Type B), or 10 kD dextran (Pharmacosmos A/S, Denmark).

The second solution or second polymer component may also include one or more additives. In one embodiment, the additive is compatible with the second polymer component and phyllosilicate nanoplatelets. In another embodiment, the additive does not contain aldehydes. Generally, the amount of additive varies depending on the application, tissue type, concentration of the second solution, concentration of the first solution, the type of second polymer component, the type of dendrimer, and/or the type of first polymer component. Examples of suitable additives, include, but are not limited to, pH modifiers, thickeners, antimicrobial agents, colorants, surfactants, radio-opaque compounds, and the other additives described herein. In other embodiments, first solution comprises a foaming agent.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water. In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the second solution or second polymer component includes one or more drugs. In such embodiments, the hydrogel composites or compositions may serve as a matrix material for controlled release of drug. The drug may be essentially any drug suitable for local, regional, or systemic administration from a quantity of the hydrogel composite or composition that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprofen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. In a particular embodiment, the drug comprises human bone morphogenetic protein 2. Other drugs are envisioned.

In other particular embodiments, the second solution or second polymer component includes one or more cells. For example, the hydrogel composite or composition may serve as a matrix material for delivering cells to a tissue site at which the hydrogel composite or composition has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Dendrimer Component

In embodiments, the second solution comprises a dendrimer. The dendrimer may be substituted with one or more functional groups, such as amines, that are capable of reacting with the one or more functional groups of the first polymer of the first polymer component.

In some embodiments, the dendrimer has amines on at least a portion of its surface groups, which are commonly referred to as "terminal groups" or "end groups." The dendrimer may have amines on from 25% to 100% of its surface groups. In some embodiments, the dendrimer has amines on 100% of its surface groups. In one embodiment, the dendrimer has amines on less than 75% of its surface groups. As used herein, the term "dendrimer" refers to any compound with a polyvalent core covalently bonded to two or more dendritic branches. In some embodiments, the polyvalent core is covalently bonded to three or more dendritic branches. In one embodiment, the amines are primary amines. In another embodiment, the amines are secondary amines. In yet another embodiment, one or more surface groups have at least one primary and at least one secondary amine.

In one embodiment, the dendrimer extends through at least 2 generations. In another embodiment, the dendrimer extends through at least 3 generations. In yet another embodiment, the dendrimer extends through at least 4 generations. In still another embodiment, the dendrimer extends through at least 5 generations. In a further embodiment, the dendrimer extends through at least 6 generations. In still a further embodiment, the dendrimer extends through at least 7 generations.

In one embodiment, the dendrimer has a molecular weight of about 1,000 to about 1,000,000 Daltons. In a further embodiment, the dendrimer has a molecular weight of about 3,000 to about 120,000 Daltons. In another embodiment, the dendrimer has a molecular weight of about 10,000 to about 100,000 Daltons. In yet another embodiment, the dendrimer has a molecular weight of about 20,000 to about 40,000 Daltons. Unless specified otherwise, the "molecular weight" of the dendrimer refers to the number average molecular weight.

Generally, the dendrimer may be made using any known methods. In one embodiment, the dendrimer is made by oxidizing a starting dendrimer having surface groups comprising at least one hydroxyl group so that at least a portion of the surface groups comprise at least one amine. In another embodiment, the dendrimer is made by oxidizing a starting generation 5 (G5) dendrimer having surface groups comprising at least one hydroxyl group so that at least a portion of the surface groups comprise at least one amine. In yet another embodiment, the dendrimer is made by oxidizing a starting G5 dendrimer having surface groups comprising at least one hydroxyl group so that about 25% to 100% of the surface groups comprise at least one amine. In a particular embodiment, the dendrimer is a G5 dendrimer having primary amines on about 25% to 100% of the dendrimer's surface groups. In a certain embodiment, the dendrimer is a G5 dendrimer having primary amines on about 25% of the dendrimer's surface groups.

In one embodiment, the dendrimer is a poly(amidoamine)-derived (PAMAM) dendrimer. In another embodiment, the dendrimer is a G5 PAMAM-derived dendrimer. In yet another embodiment, the dendrimer is a G5 PAMAM-derived dendrimer having primary amines on about 25% to 100% of the dendrimer's surface groups. In a further embodiment, the dendrimer is a G5 PAMAM-derived dendrimer having primary amines on about 25% of the dendrimer's surface groups.

In one embodiment, the dendrimer is a poly(propyleneimine)-derived dendrimer.

In some instances, the dendrimer or second solution further includes one or more additives. Generally, the amount of additive may vary depending on the application, tissue type, concentration of the dendrimer in the second solution, the type of dendrimer, concentration of the second polymer component in the second solution, the type of second polymer component, the type of first polymer component, and/or the concentration of the first polymer component in the first solution. Example of suitable additives, include but are not limited to, pH modifiers, thickeners, antimicrobial agents, colorants, surfactants, and radio-opaque compounds. Specific examples of these types of additives are described herein. In one embodiment, the dendrimer or second solution comprises a foaming additive.

In particular embodiments, the dendrimer or second solution includes one or more drugs. In such embodiments, the hydrogel composites or compositions may serve as a matrix material for controlled release of the one or more drugs. The drug may be essentially any drug suitable for local, regional, or systemic administration from a quantity of the hydrogel composite or composition that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene therapy. For example, the drug may comprise siRNA molecules to combat cancer. In a particular embodiment, the drug comprises human bone morphogenetic protein 2. Other drugs are envisioned.

In other particular embodiments, the dendrimer or second solution includes one or more cells. Alternatively or in addition, the first solution includes one or more cells. For example, in any of these embodiments, the hydrogel composites or compositions may serve as a matrix material for delivering cells to a tissue site at which the hydrogel composites or compositions have been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Formation of Hydrogel Composites and Compositions

Generally, the hydrogel composites and compositions described herein may be formed by combining the first solution and the second solution in any manner. In some embodiments, the first solution, and the second solution are combined before contacting a biological tissue. In other embodiments, the first solution, and the second solution are combined, in any order, on or in a biological tissue. In further embodiments, the first solution is applied to a first biological tissue, the second solution is applied to a second biological tissue, and the first and second biological tissues are contacted. In still a further embodiment, the first solution is applied to a first region of a biological tissue, the second solution is applied to a second region of a biological tissue, and the first and second regions are contacted.

Generally, the hydrogel composites and compositions may be applied to one or more biological tissues as an adhesive, sealant, and/or treatment. The one or more biological tissues may be diseased, damaged (e.g., dissected), healthy, or some combination thereof. In one embodiment, the hydrogel composites and compositions are applied to one or more biological tissues as an adhesive. In another embodiment, the hydrogel composites and compositions are applied to one or more biological tissues as a sealant. In a further embodiment, the hydrogel composites and compositions are applied to one or more biological tissues as a treatment. In an additional embodiment, the hydrogel composites and compositions are applied to one or more biological tissues as an adhesive and sealant. In still another embodiment, the hydrogel composites and compositions are applied to one or more biological tissues as an adhesive and treatment. In yet another embodiment, the hydrogel composites and compositions are applied to one or more biological tissues as a sealant and treatment. In a still further embodiment, the hydrogel composites and compositions are applied to one or more biological tissues as an adhesive, sealant, and treatment.

The hydrogel composites and compositions may be applied to the biological tissue using any suitable tool and methods. Non-limiting examples include the use of syringes or spatulas. Double barrel syringes with rigid or flexible discharge tips, and optional extension tubes, known in the art are envisioned.

As used herein, the hydrogel composites and compositions are a "treatment" when they improve the response of at least one biological tissue to which they are applied. In some embodiments, the improved response is lessening overall inflammation, improving the specific response at the wound site/interface of the tissue and hydrogel composites or compositions, enhancing healing, repairing torn or broken tissue, or a combination thereof. As used herein, the phrase "lessening overall inflammation" refers to an improvement of histology scores that reflect the severity of inflammation. As used herein, the phrase "improving the specific response at the wound site/interface of the tissue and hydrogel composite or compositions" refers to an improvement of histology scores that reflect the severity of serosal neutrophils. As used herein, the phrase "enhancing healing" refers to an improvement of histology scores that reflect the severity of serosal fibrosis.

In embodiments, the hydrogel composites and compositions provided herein are used as tissue adhesives, tissue sealants, tissue treatments, matrix materials, fillers, coatings, or a combination thereof. In some embodiments, the hydrogel composites and compositions are used in tissue engineering applications, including orthopedic applications, which require demanding mechanical characteristics during implantation and tissue regeneration. In other embodiments, the hydrogel composites and compositions are used at least as part of a procedure for repairing focal cartilage defects, and/or as an osteoinductive/osteocondutive "putty" for bone repair or spinal fusion. In additional embodiments, the hydrogel composites and compositions may be used in a variety of structural roles, including those that require a high strength adhesive and/or a coating. In still further embodiments, hydrogel composites and compositions can be used as a bioactive adhesive coating for drug delivery applications.

In embodiments, the hydrogel composites and compositions may be used for localized drug delivery. The drugs that may be delivered with the hydrogel composites and compositions include, but are not limited to small molecule drugs, biologics, or a combination thereof. Methods of locally delivering a drug may comprise applying to a biological tissue, such as a human tissue, a drug delivery composition as provided herein, and permitting at least one drug to diffuse from the composition into the biological tissue. The biological tissue may include osseous tissue.

In embodiments, the hydrogel composites and compositions may be used as a degradable scaffold for tissue engineering applications. The hydrogel composites and compositions may assist with guiding the infiltration and differentiation of cells to repair a tissue defect.

In embodiments, the hydrogel composites and compositions may be used in challenging or awkward implantation environments, including under flowing liquids and/or in inverted geometries.

Before or after contacting one or more biological tissues, the hydrogel composites and compositions may be allowed adequate time to cure or gel. When the hydrogel composites and compositions "cure" or "gel," as those terms are used herein, it means that the one or more functional groups of the first polymer have undergone one or more reactions with the dendrimer and/or second polymer, and one or more biological tissues. Not wishing to be bound by any particular theory, it is believed that the hydrogel composites and compositions described herein are effective because the first polymer component reacts with both (i) the dendrimer and/or second polymer component, and (ii) the surface of the biological tissues. In certain embodiments, the first polymer component's aldehyde functional groups react with the amines on (i) the dendrimer and/or second polymer component, and (ii) the biological tissues to form imine bonds. In these embodiments, it is believed that the amines on the dendrimer and/or second polymer component react with a high percentage of the aldehydes of the first polymer component, thereby reducing toxicity and increasing biocompatibility of the hydrogel composites and compositions. Typically, the time needed to cure or gel the hydrogel composites and compositions will vary based on a number of factors, including, but not limited to, the characteristics of the first polymer component, second polymer component and/or dendrimer, the concentrations of the first solution and second solution, the pH of the first and second solution, and the characteristics of the one or more biological tissues. In embodiments, the hydrogel composites and compositions will cure sufficiently to provide desired bonding or sealing shortly after the components are combined. The gelation or cure time should provide that a mixture of the components can be delivered in fluid form to a target area before becoming too viscous or solidified and then once applied to the target area sets up rapidly thereafter. In one embodiment, the gelation or cure time is less than 120 seconds. In another embodiment, the gelation or cure time is between 3 and 60 seconds. In a particular embodiment, the gelation or cure time is between 5 and 30 seconds.

In certain embodiments, one or more foaming agents are added to the first solution and/or second solution before the solutions are combined. In one embodiment, the foaming agents comprise a two part liquid system comprising Part 1 and Part 2, wherein Part 1 comprises a bicarbonate and Part 2 comprises an aqueous solution of di- or polyaldehydes and a titrant. A wide range of di- or polyaldhydes exist, and their usefulness is restricted largely by availability and by their solubility in water. For example, aqueous glyoxal (ethanedial) is useful, as is aqueous glutaraldehyde (pentadial). Water soluble mixtures of di- and polyaldehydes prepared by oxidative cleavage of appropriate carbohydrates with periodate, ozone or the like may also be useful.

A titrant is most preferably employed in the liquid solution of Part 2. More specifically, the titrant is an organic or inorganic acid, buffer, salt, or salt solution which is capable of reacting with the bicarbonate component of Part 1 to generate carbon dioxide and water as reaction by-products. The carbon dioxide gas that is generated creates a foam-like structure of the hydrogel composites and compositions and also causes the volume of the hydrogel composites and compositions to expand.

Most preferably, the titrant is an inorganic or organic acid that is present in an amount to impart an acidic pH to the resulting mixture of the Part 1 and Part 2 components. Preferred acids that may be employed in the practice of the present invention include phosphoric acid, sulfuric acid, hydrochloric acid, acetic acid, and citric acid.

Tissue Specific Formulations

Generally, the hydrogel composites and compositions may be adjusted in any manner to compensate for differences between tissues. In one embodiment, the amount of first polymer component is increased or decreased while the amount of dendrimer and/or second polymer component is unchanged. In another embodiment, the amount of dendrimer and/or second polymer component is increased or decreased while the amount of first polymer component is unchanged. In another embodiment, the concentration of the first polymer component in the first solution is increased or decreased while the second solution is unchanged. In yet another embodiment, the concentration of the dendrimer and/or second polymer component in the second solution is increased or decreased while the first solution is unchanged. In a further embodiment, the concentrations of the both the first polymer component in the first solution and the dendrimer and/or second polymer component in the second solution are changed.

When the amine density on the surface of a particular biological tissue is unknown due to disease, injury, or otherwise, an excess of the first solution may, in some embodiments, be added when the hydrogel composites and compositions are first applied, then the amount of first solution may be reduced, e.g., incrementally or drastically, until the desired effect is achieved. The "desired effect," in this embodiment, may be an appropriate or adequate curing time, adhesion, sealing, treatment, or a combination thereof. Not wishing to be bound by any particular theory, it is believed that an excess of the first solution may be required, in some instances, to obtain the desired effect when the amine density on a biological tissue is low. Therefore, adding an excess will help the user, in this embodiment, achieve adequate sealing or adhesion or treatment in less time. This is particularly desirable in emergency situations.

In other embodiments, however, a lower amount of the first solution may be added when the hydrogel composites and compositions are first applied, then the amount of first solution may be increased, e.g., incrementally or drastically, until the desired effect is achieved, which may be adequate curing time, adhesion, sealing, treatment, or a combination thereof.

In embodiments, the hydrogel composites and compositions can be optimized in view of a target biological tissue, by adjusting one or more of the following: rheology, mechanics, chemistry/adhesion, degradation rate, drug release, and bioactivity. These can be adjusted, in embodiments, by altering the type and/or concentration of phyllosilicate nanoplatelets, the type and/or concentration of the first polymer component, and type and/or concentration of the dendrimer, the type and/or concentration of the second polymer component, or a combination thereof.

Hydrogel Composite and Composition Kits

In another aspect, a kit is provided that comprises a first part that includes the first solution, and a second part that includes the second solution. The kit may further include an applicator or other device means, such as a multi-compartment syringe, for storing, combining, and delivering the two solutions and/or the resulting hydrogel composites and compositions to a tissue site.

In one embodiment, the kit comprises separate reservoirs for the first solution and the second solution. In certain embodiments, the kit comprises reservoirs for first solutions of different concentrations. In other embodiments, the kit comprises reservoirs for second solutions of different concentrations.

In one embodiment, the kit comprises instructions for selecting an appropriate concentration or amount of at least one of the first solution and/or second solution to compensate or account for at least one characteristic of one or more biological tissues. In one embodiment, the hydrogel composites and compositions are selected based on one or more predetermined tissue characteristics. For example, previous tests, may be performed to determine the number of density of bonding groups on a biological tissue in both healthy and diseased states. Alternatively, a rapid tissue test may be performed to assess the number or density of bonding groups. Quantification of tissue bonding groups can be performed by contacting a tissue with one or more materials that (1) have at least one functional group that specifically interacts with the bonding groups, and (2) can be assessed by way of fluorescence or detachment force required to separate the bonding groups and the material. In another embodiment, when the density of bonding groups on a biological tissue is unknown, an excess of the first polymer having one or more aldehydes, may be initially added as described herein to gauge the density of bonding groups on the surface of the biological tissue.

In certain embodiments, the kit comprises at least one syringe. In one embodiment, the syringe comprises separate reservoirs for the first solution and second solution. The syringe may also comprise a mixing tip that combines the two solutions as the plunger is depressed. The mixing tip may be release-ably securable to the syringe (to enable exchange of mixing tips), and the mixing tip may comprise a static mixer. In some embodiments, the reservoirs in the syringe may have different sizes or accommodate different volumes of solution. In other embodiments, the reservoirs in the syringe may be the same size or accommodate the same volumes of the solution. In a further embodiment, one reservoir may comprise Part 1 of the foaming composition described hereinabove, and a second reservoir may comprise Part 2 of the foaming composition.

Figure 1:
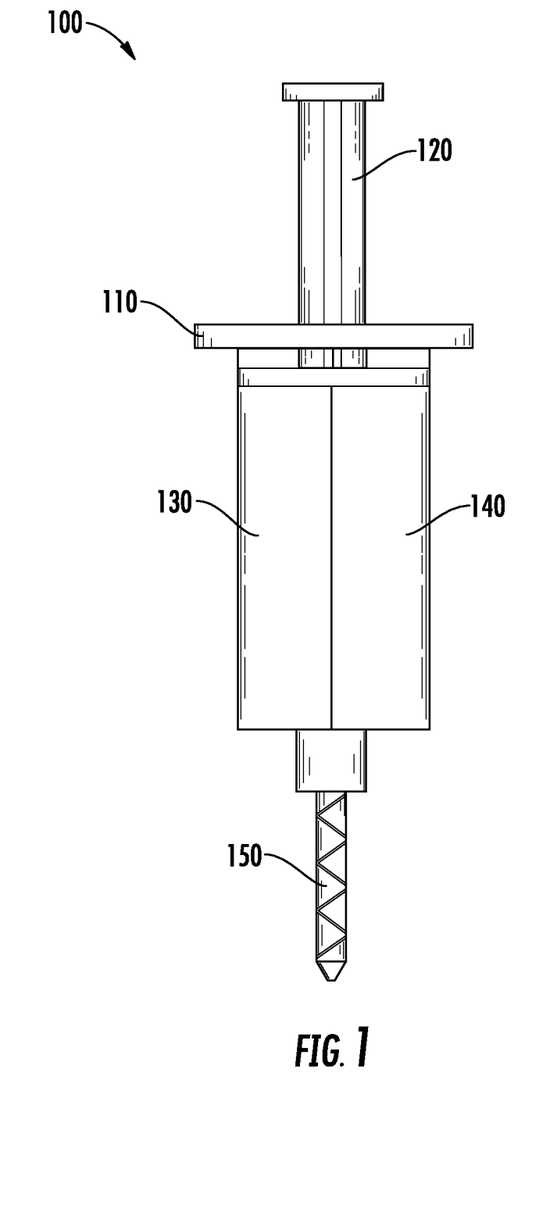
FIG. 1 depicts one embodiment of a kit containing the components of a hydrogel composite or composition.

FIG. 1 depicts one embodiment of a syringe 100. The syringe 100 includes a body 110 with two reservoirs (130, 140). A first solution is disposed in the first reservoir 130, and a second solution is disposed in the second reservoir 140. The two reservoirs (130, 140) are emptied by depressing the plunger 120, which pushes the contents of the two reservoirs (130, 140) into the mixing tip 150 and out of the syringe 100.

Figure 2:
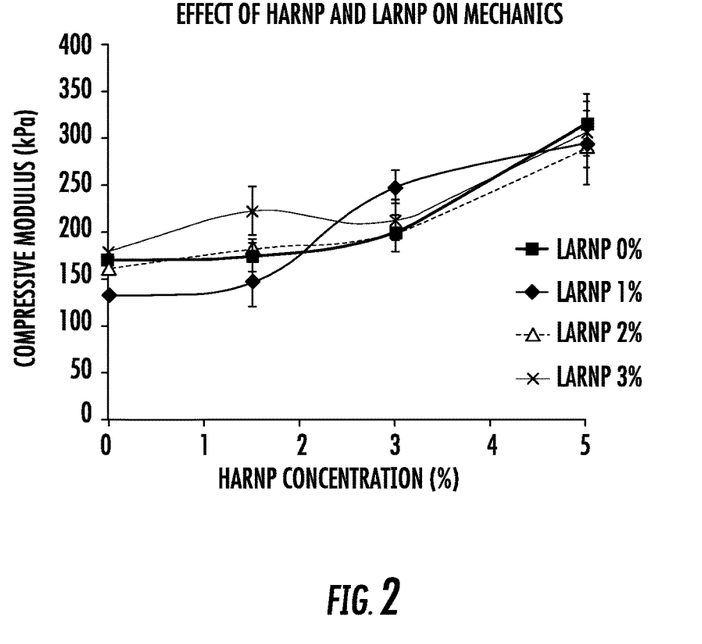
FIG. 2 depicts the effects of embodiments of high and low aspect ratio nanoplatelets on one embodiment of a hydrogel.

FIG. 2 depicts another embodiment of the components of a hydrogel nanocomposite, and a hydrogel nanocomposite.

In a further embodiment, one or more of the reservoirs of the syringe may be removable. In this embodiment, the removable reservoir may be replaced with a reservoir containing a first solution or second solution of a desired concentration.

In a preferred embodiment, the kit is sterile. For example, the components of the kit may be packaged together, for example in a tray, pouch, and/or box. The packaged kit may be sterilized using known techniques at suitable wavelengths (where applicable), such as electron beam irradiation, gamma irradiation, ethylene oxide sterilization, or other suitable techniques.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1

Effect of Nanoplatelets of Different Aspect Ratios

A series of hydrogels was made that contained 0, 1.5, 3, and 5% high aspect ratio nanoplatelets (HARNPs), and 0, 1, 2, and 3% low aspect ratio nanoplatelets (LARNPs), respectively.

The hydrogels of this example were made by combining in water the following: a macromer solution of 20% dextran-aldehyde (~50% oxidation) and a macromer solution of 24.6% generation 5 PAMAM dendrimer (25% surface amines/75% hydroxyls, Dendritech, Inc., Michigan, USA).

Differing amounts of LARNP (0, 20, 40, and 60 mg) were added to 1 mL of the dextran macromer solution and dispersed overnight. Similarly, differing amounts of HARNP (0, 30, 50, 100 mg) were added per mL of the PAMAM dendrimer solution and dispersed overnight. It was ensured that the dendrimer-HARNP solutions had a uniform pH of ~9.3 to eliminate or at least reduce HARNP-based variations in pH that can change the amine protonation state.

Following overnight dispersion, the macromer solutions were loaded into two-barrel syringes, injected through a static mixer needle, and polymerized in rubber molds for 20 minutes. Following 20 minutes, the samples were removed, measured for diameter and height, and placed on a compression plate submerged in saline inside a Biss (Karnataka, India) mechanical tester.

The samples were compressed uniaxially at 0.01 mm/s (approximately 0.25% strain/sec) for at least 50% of the strain. Stress and strain were derived from force/displacement data and geometric measurements, and an elastic modulus was calculated from the tangent to the curve at 30% strain.

As depicted at FIG. 2, the compressive modulus (kPa) of the hydrogels increased by about 100% as the concentration of the HARNPs was increased from 0% to 5%. This effect was largely independent of the addition of 0-3% of the LARNPs, as the addition of the LARNPs had no substantial effect on the mechanical reinforcement of the hydrogel composite of this example.

Figure 3A:
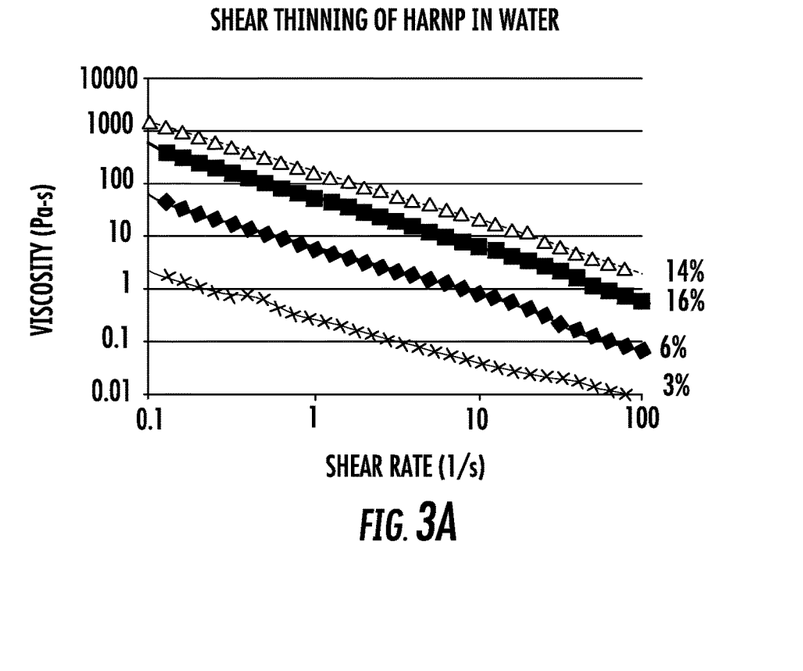
FIG. 3A depicts the shear thinning of one embodiment of a high aspect ratio nanoplatelet in water.
Figure 3B:
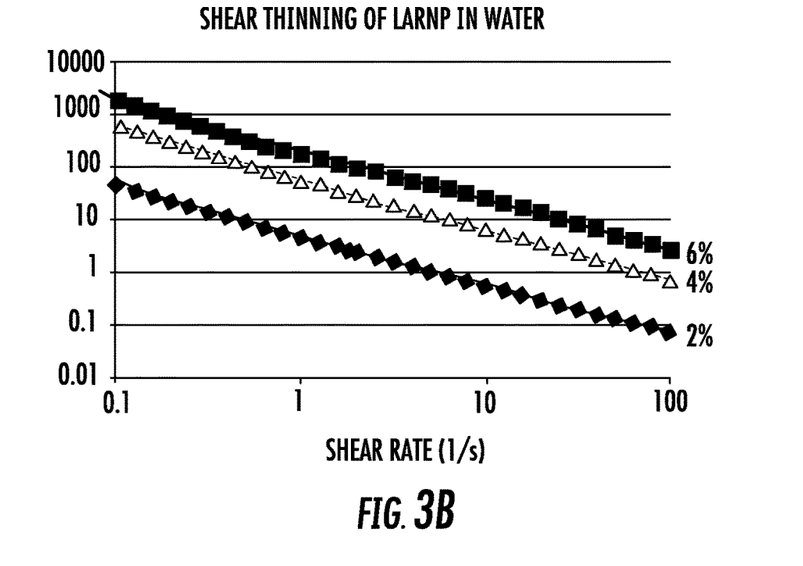
FIG. 3B depicts the shear thinning of one embodiment of a low aspect ratio nanoplatelet in water.

The shear thinning of HARNPs and LARNPs in water also was measured, as depicted at FIG. 3A and FIG. 3B. For the shear thinning tests, LARNPs and HARNPs were dispersed in water overnight at varying concentrations (LARNPs up to 6%, HARNPs up to 14%; these values were based on their maximum dispersability). Following dispersion, the solutions were loaded onto a rheometer (TA Instruments AR2000; DE, USA) with a 25 mm parallel plate fixture. The samples were maintained at 37° C. using a Peltier plate, and allowed to equilibrate for five minutes prior to testing. Shear thinning tests were performed by rotation at a constant shear rate until equilibrium viscosity was reached; the steady state viscosity at each shear rate ranging from 0.1-100 1/s was collected.

Figure 4:
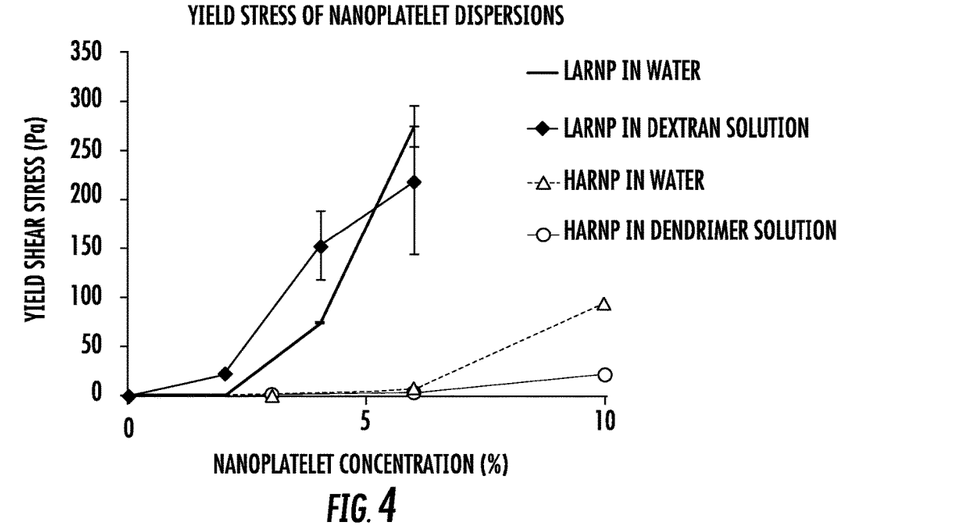
FIG. 4 depicts the yield shear stress of various embodiments of nanoplatelet dispersions.

Also, the yield stress of various nanoplatelet dispersions was measured, including LARNPs in water, LARNPs in a dextran solution, HARNPs in water, and HARNPs in a dendrimer solution, as shown at FIG. 4. Macromer solutions of 20% dextran-aldehyde and 24.6% PAMAM dendrimer were prepared as above and LARNPs and HARNPs were added as necessary. The samples were loaded onto the rheometer, heated, and allowed to equilibrate. The strain rate was slowly increased until the shear stress hit a peak and started to decrease. This initial peak in shear stress was treated as the yield stress.

The foregoing data revealed that both of the HARNPs and LARNPs of this example increased viscosities and imparted shear thinning properties to the solutions of this example in a dose dependent manner. In this particular example, it was observed that LARNPs achieved higher viscosities at lower concentrations, and it was observed that the LARNPs of this example imparted a substantial yield stress to both water and a macromer dispersions at lower concentrations than the HARNPs of this example.

Example 3

Biocompatibility of Hydrogel Composites

The biocompatibility of several embodiments of hydrogel composites was tested. First, an in vitro assessment of cytocompatibility with mouse mesenchymal cells with and without nanoplatelets was conducted.

Figure 5:
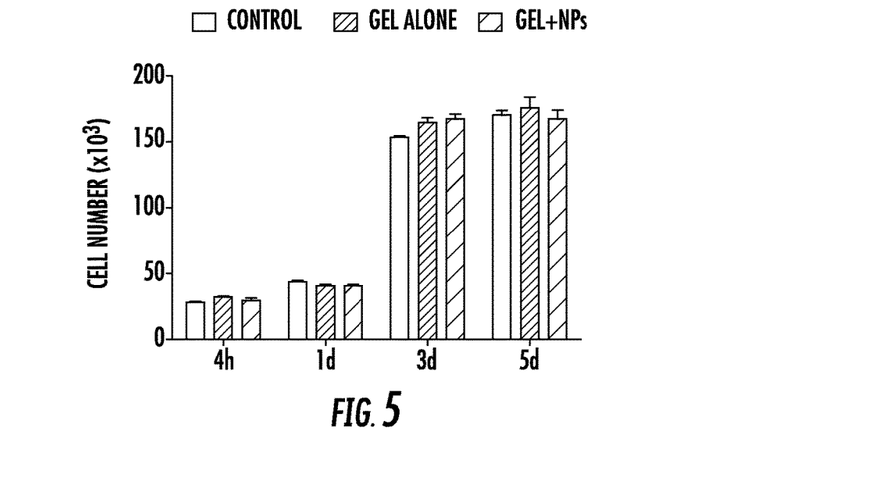
FIG. 5 depicts cell numbers obtained upon exposure to one embodiment of a hydrogel and one embodiment of a hydrogel composite containing nanoplatelets.

Over 5 days, the materials showed excellent cytocompatibility by live (green) and dead (red) staining, as well as by cell growth (see FIG. 5). When implanted in the mouse subcutaneous space, the hydrogel composites evidenced excellent material-tissue integration, with extensive cell infiltration at 7 and 28 days.

In this example, mouse mesenchymal cells were cultured in standard conditions. They were plated onto a 24-well plate and hydrogel composites were placed in direct contact with the cells (the hydrogels were formed from a solution that included 20% dextran-aldehyde (Example 1) and a solution that included 24.6% dendrimer (Example 1) with and without LARNP and HARNP, respectively—typical concentrations were ~4% LARNP and ~6% HARNP).

Following 1 and 5 days, the cells were stained with live/dead stain (green=live, red=dead) to determine overall cell viability. In addition, the cell number was quantified by an MTT assay.

Following in vitro cytocompatibility testing, the same hydrogel composites (50-100 ul) were doped with fluorescent labels, and implanted subcutaneously in mice for up to 28 days. The animals were sacrificed at 3, 7, and 28 days, and their tissue was analyzed by cryosectioning, DAPI (4',6'-diamidino-2-phenylindole) staining for nuclei, and fluorescent microscopy.

Example 4

Regeneration of Calvarial Defects

In mice, 3.5 mm calvarial defects were induced with either a control hydrogel composite, a hydrogel composite containing recombinant human bone morphogenetic protein 2 (rhBMP2), or a collagen sponge positive control (Helistat) containing an identical dose of rhBMP2.

Figure 6:
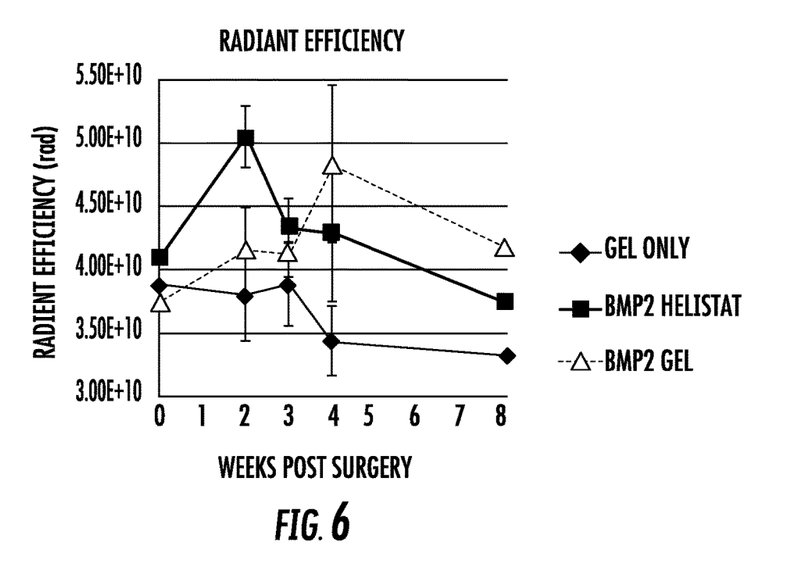
FIG. 6 depicts the radiant efficiency produced by various embodiments of hydrogels and hydrogel composites at certain weeks after surgery.
Figure 7:
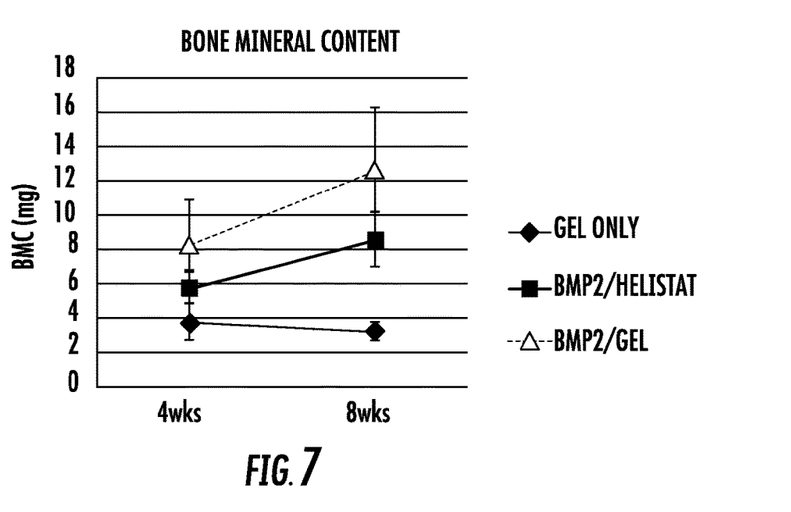
FIG. 7 depicts the bone mineral content recorded after 4 weeks and 8 weeks after exposure to an embodiment of a hydrogel composite, and other materials.

Over 8 weeks, rhBMP2/hydrogel composite and rhBMP2/Helistat showed excellent healing of the calvarial defect, as evidenced by in vivo measurements of osterix expression (an important osteogenic transcription factor; radiant efficiency (FIG. 6)), and bone mineral content (FIG. 7), as well as histological endpoints. These results were believed to validate the ability of this embodiment of the hydrogel composite to be readily implanted into tissue, and to act as a carrier of growth factors for bone repair applications.

In this example, gel-mediated healing of bone was evaluated in a mouse calvarial defect model. Osterix-mCherry mice (which fluoresce upon expression of osterix, an important transcription factor in early osteogenesis) had 3.5 mm full thickness bilateral defects drilled into the parietal bone of the calvarium. The defects were filled with bone morphogenetic protein 2 (BMP-2) loaded hydrogel composites (10 ul; typically 20% dextran (Example 1), 40 mg LARNP/ml, 24.6% PAMAM dendrimer (Example 1) with 60 mg HARNP/ml and 2 ug rhBMP-2 per defect). Controls included a hydrogel composite that did not contain BMP-2, and a collagen sponge that contained an identical dose of BMP-2.

The animals were imaged by IVIS periodically following the surgery to Osterix-mCherry expression. Bone mineralization was followed over time by microCT. Following 8 weeks, the animals were sacrificed and calvaria were analyzed by histology (decalcification/fixation, cryosectioning, staining by Masson's Trichrome).

Example 5

Use of Hydrogel Composites in Regeneration of Segmental Bone Defects

Segmental bone defect regeneration was evaluated in a rat femoral segmental bone defect model. Femurs of Sprague-Dawley rats were isolated and a 5 mm full-thickness defect was created by drilling. Bones were fixed in place using surgical screws and a plastic bar. The defects were untreated, or filled with hydrogel composites (20% dextran (Example 1) with 60 mg/ml LARNPs, 24.6% PAMAM dendrimer (Example 1) with 100 mg/ml HARNPs) or collagen sponges (Helistat) loaded with 12 μg rhBMP-2 per defect. The animals were imaged over time using Faxitron radiography and sacrificed at 12 weeks.

Following 12 weeks of regeneration, radiographs of both Helistat/BMP2 and hydrogel/BMP2 conditions showed extensive mineralization in the defect area, but untreated defects were unchanged. This was believed to validate the ability of one embodiment of the hydrogel composite to be readily implanted into tissue and act as a carrier of growth factors for more challenging bone repair applications.

Example 6

Osteochondral Defect Repair

Osteochondral defect repair was demonstrated in a rabbit OC defect model. New Zealand White rabbit legs were shaved, opened, and the patella was subluxed to expose the trochlear groove. A 3 mm diameter×3 mm depth defect was created in the trochlea, and was filled by either a BMP-2 loaded collagen sponge or hydrogel composite (Dextran 20% (Example 1) with 60 mg/ml LARNP, PAMAM dendrimer 24.6% (Example 1) with 120 mg/ml HARNP). Following 8 weeks, the animals were sacrificed and analyzed by histology (decalcification/fixation, cryosectioning, Safranin O/Fast Green staining).

Safranin O/fast green staining of the hydrogel composite alone showed excellent material-tissue integration but no appreciable cartilage repair, along with significant loss of glycosaminoglycans in adjacent tissue. With the addition of rhBMP-2, the hydrogel composite of this example was completely degraded in the same time period, leaving behind a GAG-rich cartilage surface and a mostly reconstituted subchondral layer. For comparison, a positive control with a collagen sponge soaked in an identical dose of rhBMP-2 was tested, evidencing excellent GAG expression but poor tissue cohesion at the defect site.

We claim:

1. A method for treating, adhering, or sealing biological tissue, the method comprising:
    providing a first solution comprising low aspect ratio phyllosilicate nanoplatelets and a first polymer component, the first polymer component comprising a first polymer having one or more aldehydes;
    providing a second solution comprising high aspect ratio phyllosilicate nanoplatelets and at least one of (i) a dendrimer comprising at least two branches with one or more surface groups, wherein about 25% to 100% of the surface groups comprise at least one primary or secondary amine, and (ii) a second polymer component comprising a second polymer having one or more amines;
    combining the first and second solutions together to produce a hydrogel composite; and
    contacting one or more biological tissues with the hydrogel composite.

2. The method of claim 1, wherein (i) the low aspect ratio phyllosilicate nanoplatelets are substantially evenly dispersed in the first solution, (ii) the high aspect ratio phyllosilicate nanoplatelets are substantially evenly dispersed in the second solution, or (iii) both the low aspect ratio phyllosilicate nanoplatelets and the high aspect ratio phyllosilicate nanoplatelets are substantially evenly dispersed in the first solution and the second solution, respectively.

3. The method of claim 1, wherein at least one of the low aspect ratio phyllosilicate nanoplatelets and the high aspect ratio phyllosilicate nanoplatelets is present in the first solution and the second solution, respectively, at a concentration of about 0.01% to about 30% by weight of the first solution or the second solution, respectively.

4. The method of claim 1, wherein a portion of at least one of the low aspect ratio phyllosilicate nanoplatelets and the high aspect ratio phyllosilicate nanoplatelets of the first solution and the second solution, respectively, is substituted with functionalized cations.

5. The method of claim 1, wherein the concentration of the first polymer component in the first solution is about 0.01 percent to about 30 percent, by weight of the first solution.

6. The method of claim 1, wherein the first polymer has a molecular weight of about 1,000 to about 1,000,000 Da.

7. The method of claim 1, wherein the first polymer has a degree of functionalization of about 10% to about 75%.

8. The method of claim 1, wherein the first polymer comprises a nonionic polysaccharide.

9. The method of claim 8, wherein the nonionic polysaccharide comprises dextran, dextrin, cellulose, derivatives thereof, or a combination thereof.

10. The method of claim 1, wherein the first polymer comprises an anionic polysaccharide.

11. The method of claim 10, wherein the anionic polysaccharide comprises hyaluronic acid, chondroitin sulfate, alginate, cellulose gum, or a combination thereof.

12. The method of claim 1, wherein the first polymer comprises a cationic polysaccharide.

13. The method of claim 12, wherein the cationic polysaccharide comprises chitosan, cationic guar gum, cationic hydroxyethylcellulose, a polysaccharide modified with trimethylammonium groups, or a combination thereof.

14. The method of claim 1, wherein the first polymer comprises a hydrophilic polymer.

15. The method of claim 14, wherein the hydrophilic polymer is modified with polyester groups.

16. The method of claim 14, wherein the hydrophilic polymer comprises poly(vinyl alcohol), poly(acrylic acid), poly(acrylamide), poly(ethylene oxide), or a combination thereof.

17. The method of claim 1, wherein the first polymer comprises a hydrophobic polymer.

18. The method of claim 17, wherein the hydrophobic polymer comprises pendant hydrophilic polymers.

19. The method of claim 17, wherein the hydrophobic polymer comprises polycaprolactam, poly(lactic acid), polycaprolactone, or a combination thereof.

20. The method of claim 1, wherein the dendrimer component is present in the second solution at a concentration of about 0.01% to about 30%, by weight of the second solution.

21. The method of claim 1, wherein the dendrimer comprises a PAMAM dendrimer.

22. The method of claim 1, wherein the second polymer component is present in the second solution at a concentration of about 0.01% to about 30% by weight of the second solution.

23. The method of claim 1, wherein the total concentration of the second polymer component and the dendrimer in the second solution is about 0.01% to about 40% by weight of the second solution.

24. The method of claim 1, wherein the second polymer is a polyamine.

25. The method of claim 24, wherein the polyamine comprises amine-terminated multi-arm poly(ethylene oxide), polyethyleneimine, or a combination thereof.

26. The method of claim 1, wherein the second polymer comprises chitosan, collagen, gelatin, or a combination thereof.

27. The method of claim 1, wherein the first solution and the second solution are combined on a biological tissue.

28. The method of claim 1, wherein the first solution and the second solution are combined in a tip of a syringe.

29. The method of claim 1, wherein the second solution is applied to a tissue followed by the first solution.

30. The method of claim 1, wherein the one or more biological tissues comprise human tissue.

31. The method of claim 1, wherein the first solution, the second solution, or both further comprise an additive selected from the group consisting of foaming agents, pH modifiers, thickeners, antimicrobial agents, colorants, surfactants, and radio-opaque agents.

32. The method of claim 1, wherein at least one of the first solution and the second solution comprises a drug.

33. The method of claim 1, wherein at least one of the first solution and the second solution further comprises stem cells or other cells.

* * * * *